(12) United States Patent
Bonde

(10) Patent No.: US 10,729,834 B2
(45) Date of Patent: Aug. 4, 2020

(54) HEART FAILURE RECOVERY DEVICE AND METHOD OF TREATMENT

(71) Applicant: Yale University, New Haven, CT (US)

(72) Inventor: Pramod Bonde, Woodbridge, CT (US)

(73) Assignee: Yale University, New Haven, CT (US)

( * ) Notice: Subject to any disclaimer, the term of this patent is extended or adjusted under 35 U.S.C. 154(b) by 377 days.

(21) Appl. No.: 15/535,494

(22) PCT Filed: Dec. 17, 2015

(86) PCT No.: PCT/US2015/066256
§ 371 (c)(1),
(2) Date: Jun. 13, 2017

(87) PCT Pub. No.: WO2016/100600
PCT Pub. Date: Jun. 23, 2016

(65) Prior Publication Data
US 2019/0001037 A1    Jan. 3, 2019

Related U.S. Application Data

(60) Provisional application No. 62/094,460, filed on Dec. 19, 2014.

(51) Int. Cl.
*A61M 1/12* (2006.01)
*A61M 1/10* (2006.01)

(52) U.S. Cl.
CPC .......... *A61M 1/127* (2013.01); *A61M 1/1029* (2014.02); *A61M 1/1087* (2014.02);
(Continued)

(58) Field of Classification Search
CPC .. A61M 1/127; A61M 1/1096; A61M 1/1029; A61M 1/1087; A61M 1/122;
(Continued)

(56) References Cited

U.S. PATENT DOCUMENTS 4,673,394 A * 6/1987 Fenton, Jr. ........ A61M 5/14276
128/912
5,941,813 A * 8/1999 Sievers ............... F04D 13/0673
600/16
(Continued)

FOREIGN PATENT DOCUMENTS

WO    2014141284 A2    9/2014
WO    2014145667 A2    9/2014

OTHER PUBLICATIONS

A. P. Sample, D. T. Meyer and J. R. Smith, "Analysis, Experimental Results, and Range Adaptation of Magnetically Coupled Resonators for Wireless Power Transfer," in IEEE Transactions on Industrial Electronics, vol. 58, No. 2, pp. 544-554, Feb. 2011. doi: 10.1109/TIE.2010.2046002.

(Continued)

*Primary Examiner* — Christopher Koharski
*Assistant Examiner* — James Moss
(74) *Attorney, Agent, or Firm* — Riverside Law LLP

(57) ABSTRACT

A heart failure recovery device includes a fluid pump having an inlet and an outlet in fluid communication with a pump reservoir, and a pumping element disposed within the pump reservoir, the pumping element including a protrusion that in an active state is configured to rotate and move fluid away from the inlet and towards the outlet. A receiver coil can be electrically coupled to the fluid pump and is configured to subcutaneously absorb electromagnetic energy for powering the fluid pump. In certain embodiments, an implantable port provides fluid access to the pump reservoir for cleaning and maintaining the fluid pump. In other embodiments, a valve closes fluid access to at least one of the inlet and the outlet during periods when the device is not being used for treatment.

23 Claims, 3 Drawing Sheets

(52) U.S. Cl.
CPC .......... *A61M 1/1096* (2014.02); *A61M 1/122* (2014.02); *A61M 1/101* (2013.01); *A61M 1/102* (2014.02); *A61M 1/1005* (2014.02); *A61M 1/1037* (2013.01); *A61M 1/1086* (2013.01); *A61M 2205/3327* (2013.01); *A61M 2205/8206* (2013.01); *A61M 2205/8243* (2013.01); *A61M 2230/04* (2013.01)

(58) Field of Classification Search
CPC ........ A61M 2205/8243; A61M 1/1005; A61M 1/102; A61M 1/1086; A61M 1/1037; A61M 1/101; A61M 2230/04; A61M 2205/8206; A61M 2205/3327
See application file for complete search history.

(56) References Cited

U.S. PATENT DOCUMENTS

| | | | |
|---|---|---|---|
| 6,146,325 A * | 11/2000 | Lewis | A61M 1/1008 600/16 |
| 8,299,652 B2 | 10/2012 | Sample | |
| 2011/0201870 A1 | 8/2011 | Forsell | |
| 2013/0041203 A1 | 2/2013 | Heilman | |
| 2013/0310630 A1 | 11/2013 | Smith | |
| 2014/0163307 A1 | 6/2014 | Zilbershlag | |
| 2014/0336444 A1 * | 11/2014 | Bonde | A61M 1/1086 600/16 |

OTHER PUBLICATIONS

B. H. Waters, A. P. Sample, P. Bonde and J. R. Smith, "Powering a Ventricular Assist Device (VAD) With the Free-Range Resonant Electrical Energy Delivery (FREE-D) System," in Proceedings of the IEEE, vol. 100, No. 1, pp. 138-149, Jan. 2012. doi: 10.1109/JPROC.2011.2165309.

Lund LH, Edwards LB, Kucheryavaya AY, et al. The Registry of the International Society for Heart and Lung Transplantation: Thirty-first Official Adult Heart Transplant Report—2014; Focus Theme: Retransplantation. The Journal of Heart and Lung Transplantation 2014;33(10):996-1008. doi:10.1016/j.healun.2014.08.003.

Go AS, Mozaffarian D, Roger VL, et al. Heart Disease and Stroke Statistics—2013 Update A Report From the American Heart Association. Circulation 2013;127(1):e6-e245. doi:10.1161/CIR.0b013e31828124ad.

MD DLM. Heart Failure: A Companion to Braunwald's Heart Disease: Expert Consult—Online and Print, 2e. 2 edition. Philadelphia: Saunders; 2010.

Kirklin JK, Naftel DC, Kormos RL, et al. Fifth INTERMACS annual report: risk factor analysis from more than 6,000 mechanical circulatory support patients. J. Heart Lung Transplant. 2013;32(2):141-156. doi:10.1016/j.healun.2012.12.004.

Bellumkonda L, Bonde P. Ventricular assist device therapy for heart failure—past, present, and future. Int Anesthesiol Clin 2012;50(3):123-145. doi:10.1097/AIA.0b013e31826233a9.

Asgari SS, Bonde P. Implantable physiologic controller for left ventricular assist devices with telemetry capability. J. Thorac. Cardiovasc. Surg. 2013. doi:10.1016/j.jtcvs.2013.09.012. (11 pages).

Wang JX, Smith Jr, Bonde P. Energy transmission and power sources for mechanical circulatory support devices to achieve total implantability. Ann. Thorac. Surg. 2014;97(4):1467-1474. doi:10.1016/j.athoracsur.2013.10.107.

Waters B, Sample A, Smith J, Bonde P. Toward total implantability using free-range resonant electrical energy delivery system: achieving untethered ventricular assist device operation over large distances. Cardiol Clin 2011;29(4):609-625. doi:10.1016/j.ccl.2011.08.002.

Waters BH, Smith Jr, Bonde P. Innovative Free-range Resonant Electrical Energy Delivery system (FREE-D System) for a ventricular assist device using wireless power. ASAIO J. 2014;60(1):31-37. doi:10.1097/MAT.0000000000000029.

Meyns B, Klotz S, Simon A, et al. Proof of concept: hemodynamic response to long-term partial ventricular support with the synergy pocket micro-pump. J. Am. Coll. Cardiol. 2009;54(1):79-86. doi:10.1016/j.jacc.2009.04.023.

Jeevanandam V. Are we ready to implant left ventricular assist devices in "less sick" patients? Semin. Thorac. Cardiovasc. Surg. 2012;24(1):8-10. doi:10.1053/j.semtcvs.2012.04.003.

Morley D, Litwak K, Ferber P, et al. Hemodynamic effects of partial ventricular support in chronic heart failure: results of simulation validated with in vivo data. J. Thorac. Cardiovasc. Surg. 2007;133(1):21-28. doi:10.1016/j.jtcvs.2006.07.037.

J A, Stepanoff, Ph.D. Centrifugal and Axial Flow Pumps: Theory, Design, and Application. 2 edition. Malabar, Fla: Krieger Publishing Company; 1993.

Adams DH, Popma JJ, Reardon MJ, et al. Transcatheter Aortic-Valve Replacement with a Self-Expanding Prosthesis. New England Journal of Medicine 2014;370(19):1790-1798. doi:10.1056/NEJMoa1400590.

Vandenberghe S, Shu F, Arnold DK, Antaki JF. A simple, economical, and effective portable paediatric mock circulatory system. Proc Inst Mech Eng H 2011 ;225(7):648-656.

Valdovinos J, Shkolyar E, Carman GP, Levi DS. In Vitro Evaluation of an External Compression Device for Fontan Mechanical Assistance. Artif Organs 2013. doi:10.1111/aor.12152. (9 pages).

Dixon JA, Spinale FG. Large animal models of heart failure: a critical link in the translation of basic science to clinical practice. Circ Heart Fail 2009;2(3):262-271. doi:10.1161/CIRCHEARTFAILURE.108.814459.

* cited by examiner

HEART FAILURE RECOVERY DEVICE AND METHOD OF TREATMENT

CROSS-REFERENCE TO RELATED APPLICATIONS

This application claims priority to PCT international application no. PCT/US15/66256 filed on Dec. 17, 2015, which claims priority to U.S. provisional application No. 62/094,460 filed on Dec. 19, 2014, both of which are incorporated herein by reference in their entireties.

BACKGROUND OF THE INVENTION

Current therapeutic options for end stage heart failure patients are primarily focused on palliative and hospice care. Unfortunately, heart transplantation and left ventricular assist device (LVAD) therapy is restricted to approximately 2,500 patients each year. LVAD therapy, which provides full circulatory support for heart failure patients, comes at the price of invasiveness, 24-hour care, and reduced quality of life for the remainder of the patient's life. Current LVAD devices are used as a permanent solution for heart failure and are cumbersome due to the restrictions posed on the patient. As a result, the majority of patients who present with heart failure are not considered LVAD candidates. Thus, there is a large group of patients with heart failure who do not have any other option but medications only. A large number of otherwise potential candidates are considered surgically high risk, while others are turned down for permanent therapy due to lack of family or long-term support. For patient's that require more temporary treatment, LVADs can be used as a bridge to implantation or an alternative heart failure treatment.

One of the major characteristics of patients with heart failure is repeated hospital admission with heart failure decompensation separated by intervals of stable periods. Heart failure is characterized by episodes of circulatory decompensation followed by phases of recovery until the onset of end organ dysfunction. Hemodynamic recovery mandates hospital admission and medical therapy targeted at relieving heart failure symptoms rather than increasing cardiac output. These patients are usually managed by diuresis and optimizing their cardiac function followed by discharge. Therefore, a need exists in the art for a heart failure recovery device and therapy that more effectively and efficiently addresses failing cardiac output of heart failure patients, and further, minimizes hospital readmission rates for heart failure patients. Further, a need exist for a device that is less cumbersome than traditional LVADs for patients that need temporary treatment of heart failure as a bridge to a transplant or an alternative therapy.

SUMMARY OF THE INVENTION

A large population of heart failure patients need only a modest increase in cardiac index during the decompensation phases to avoid hospital readmission. A minimally invasive HFR device designed to give modest and temporary circulatory support to the patient during these decompensation phases to avoid hospital readmission is described herein. Once stable, the HFR device can be switched off and isolated from blood circulation. This cycle can be repeated as needed, and the device can be activated only when needed.

In one aspect, the invention is a heart failure recovery device including a fluid pump having an inlet and an outlet in fluid communication with a pump reservoir, and a pumping element disposed within the pump reservoir. The pumping element has a protrusion that in an active state is configured to rotate and move fluid away from the inlet and towards the outlet. A receiver coil is electrically coupled to the fluid pump, the receiver coil configured to subcutaneously absorb electromagnetic energy for powering the fluid pump.

According to another embodiment, the invention is a heart failure recovery device including a fluid pump having an inlet and an outlet in fluid communication with a pump reservoir, and a pumping element disposed within the pump reservoir. The pumping element has a protrusion that in an active state is configured to rotate and move fluid away from the inlet and towards the outlet. An opening is in fluid communication with at least one of the inlet and the outlet, the opening fluidly sealed by a valve that opens in the active state and closes in an inactive state.

According to another embodiment, the invention is a heart failure recovery device including a fluid pump having an inlet and an outlet in fluid communication with a pump reservoir, and a pumping element disposed within the pump reservoir. The pumping element has a protrusion that in an active state is configured to rotate and move fluid away from the inlet and towards the outlet. A port has a port reservoir and a port opening fluidly sealed by an elastomeric septum and a flexible conduit having a lumen. The conduit is coupled to the fluid pump and the port, and the port reservoir and the pump reservoir are in fluid communication via the lumen.

According to another embodiment, the invention is a method for treating heart failure including implanting a heart failure recovery device at the apex of a left ventricle of a human heart, the heart failure recovery device including a fluid pump having an inlet and an outlet in fluid communication with a pump reservoir, and a pumping element disposed within the pump reservoir, the pumping element has a protrusion that in an active state is configured to rotate and move fluid away from the inlet and towards the outlet. The method includes the steps of detecting a first decompensation phase condition, setting the fluid pump to the active state based on the detecting the first decompensation phase condition, detecting a first stabilization condition, and setting the fluid pump to an inactive state based on the detecting the first stabilization condition.

According to another embodiment, the invention is a method for treating heart failure including implanting a heart failure recovery device at the apex of a left ventricle of a human heart, the heart failure recovery device including a fluid pump having an inlet and an outlet in fluid communication with a pump reservoir, and a pumping element disposed within the pump reservoir, the pumping element having a protrusion that in an active state is configured to rotate and move fluid away from the inlet and towards the outlet, and a port comprising a port reservoir and a port opening fluidly sealed by an elastomeric septum, where the port reservoir and the pump reservoir are fluidly connected by a flexible conduit comprising a lumen, and where the port reservoir is in fluid communication with the pump reservoir via the lumen. The method includes the steps of advancing a tip of a port access needle into the port reservoir, flushing a fluid from the port access needle into the port reservoir and the pump reservoir, and withdrawing the tip of port access needle from the port reservoir.

BRIEF DESCRIPTION OF THE DRAWINGS

The foregoing purposes and features, as well as other purposes and features, will become apparent with reference to the description and accompanying figures below, which are included to provide an understanding of the invention and constitute a part of the specification, in which like numerals represent like elements, and in which.

DETAILED DESCRIPTION OF THE INVENTION

Figure 1:
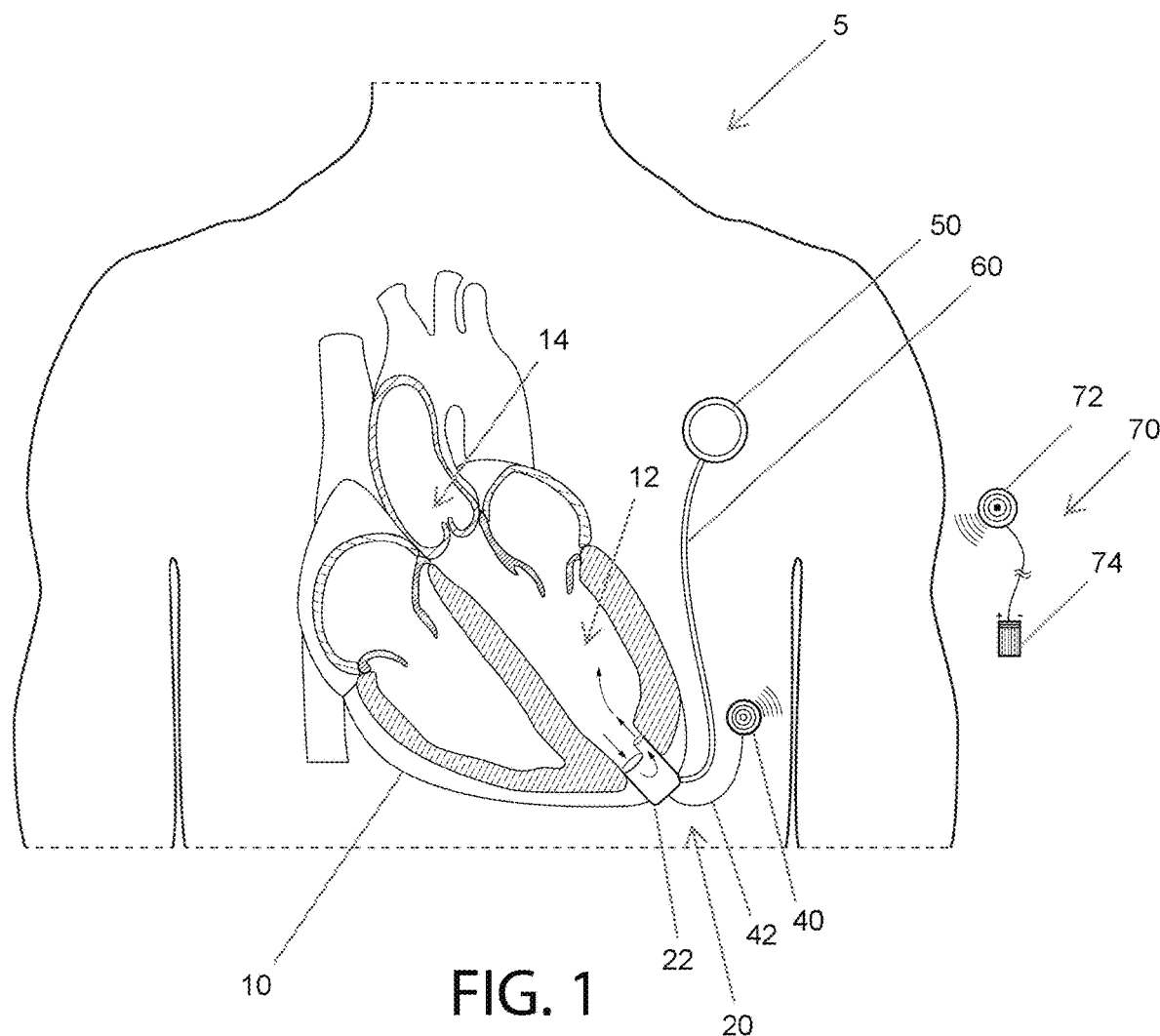
FIG. 1 is a diagram of an exemplary HFR device implanted in the heart of a patient, and a wireless power unit associated therewith.

The present invention can be understood more readily by reference to the following detailed description, the examples included therein, and to the Figures and their following description. The drawings, which are not necessarily to scale, depict selected preferred embodiments and are not intended to limit the scope of the invention. The detailed description illustrates by way of example, not by way of limitation, the principles of the invention. The skilled artisan will readily appreciate that the devices and methods described herein are merely examples and that variations can be made without departing from the spirit and scope of the invention. It is also to be understood that the terminology used herein is for the purpose of describing particular embodiments only and is not intended to be limiting.

Referring now in detail to the drawings, in which like reference numerals indicate like parts or elements throughout the several views, in various embodiments, presented herein is a heart failure recovery device and therapeutic method.

FIG. 1 shows a diagram of a HFR device 20 implanted in a patient 5. The device 20 is implanted in the heart 10 of a subject 5 at the apex of the left ventricle 12. In certain embodiments, the top of the fluid pump 22 has a step tip or staggered tip configuration. This configuration offsets the inlet of the pump 22 from the outlet of the pump 22 to minimize the recirculation of blood, and maximize the flow rate of blood out of the left ventricle 12 and through the aortic valve 14. The fluid pump 22 is powered by a wireless power system, such as, for example, the system as described in U.S. Pat. No. 8,299,652; U.S. Patent Application Publication No. 2013/0310630; Sample et al., 2011, IEEE Transactions, 58(2): 544-554; and Waters et al., 2012, Proceedings of the IEEE, 100(1): 138-149; the entire disclosures of which are incorporated by reference herein in their entireties. Certain details of a system utilizing internal components and external components according to the various embodiments described herein are shown in the exemplary system of FIG. 4.

Figure 4:
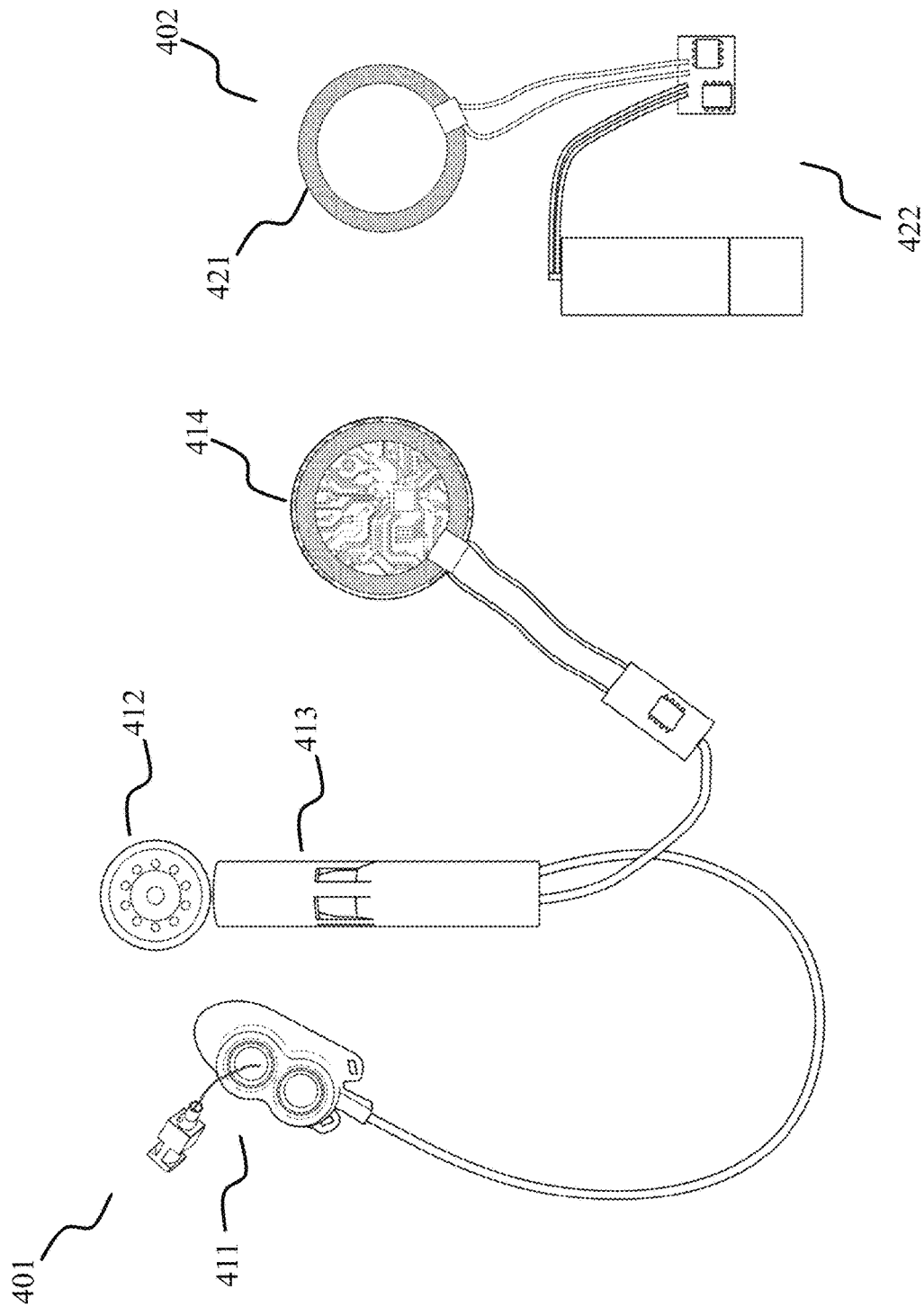
FIG. 4 shows a system including internal and external components according to an aspect of the present invention.

With reference to FIG. 4, an exemplary full system with implantable (internal) components 401 and external components 402 is shown. The implantable components 401 include a purging system 411, an iris valve 412, a pump 413, and a receive coil/controller 414. The external components 402 include a transmit coil 421 and a battery and electronics 422.

With reference back to FIG. 1, the device 20, including the fluid pump 22 and an associated controller (not shown) mounted on or within the fluid pump 22 can be powered and charged by energy transfer using magnetically coupled resonators. Magnetically coupled resonators induce power transfer between two components through the matching of the resonance frequency between a source resonator (e.g. external coil 72) and a receiver resonator (e.g. receiver coil 40). In certain embodiments, the external coil 72 sends energy to the receiver coil 40 for charging a rechargeable battery electrically coupled to the device 20 for powering the controller and the fluid pump 22. The rechargeable battery can be used as one or both of a primary battery or a backup battery. In other embodiments, the receiver coil 40 powers the controller and the fluid pump 22 by energy transferred directly from the external coil 72, powered by an external primary battery 74. As a more detailed example, an external resonator is a coil induced to resonate at a given frequency. A frequency-matched receiver resonator, within some proximity of the source, is a coil tuned to resonate at the same frequency as the source. Thus, when the source resonator is induced to resonate at the given frequency, the frequency-matched receiver resonator is also induced to resonate, which results in the transfer of power to a component attached to the receiver resonator. For example, in one embodiment, the controller comprises a receiver resonator, or is otherwise attached to a receive resonator, for wirelessly powering the controller. In another embodiment, the invention comprises a source resonator that is magnetically coupled to the receiver resonator.

In certain embodiments, the fluid pump has an integral controller. In one embodiment, the controller is a wireless controller and is sized and shaped to be implanted within the body of the user. As such, it eliminates the need for wires connecting the pump to an extracorporeal unit. In certain embodiments, the controller is implanted subcutaneously. The controller is sized and shaped to be a compact unit, thereby allowing for easier integration with the pump or implantation in the body. It should be appreciated that there is no limitation to the particular dimensions of the controller, provided the controller is implantable and retains all desired functionality as contemplated herein. In one embodiment, the controller includes an integral power source. For example, the controller may have a long-lasting battery. In another embodiment, the power source is a rechargeable power source, such as a rechargeable battery. In one embodiment, the power source is wirelessly rechargeable. The controller of the invention is not limited to any particular type of power source, but rather encompasses any type of suitable power source as would be understood by those skilled in the art.

The controller of the invention controls the function of a heart pump in order to provide a desired blood flow in the user. For example, the controller comprises a drive unit which communicates with the pump to drive the pump motor and rotating pump element, thereby controlling blood flow. Accordingly, the implanted controller communicatively connected to the heart pump, such that it sends instructional signals to the heart pump to direct the functionality of the pump. In some embodiments, the controller wirelessly communicates with the heart pump. In other embodiments, the controller is connected to the heart pump via direct wirelines. In other embodiments, the controller is integrated into the housing of the heart pump and is therefore directly connected into the circuitry of the heart pump. In one embodiment, the controller has two modes, continuous flow and pulsatile flow. In the continuous flow mode, the pump speed is adjustable using a user interface of an external control unit by the user or clinician. In the pulsatile flow mode, the pump speed is specifically attuned for the systole and diastole periods of the cardiac cycle of the user. For example, the pump speed is specifically adjusted during systole and diastole such that blood flow is varied during the cardiac cycle. The determination of systole and diastole, and the control of pump speed during the respective periods can be made in a variety of ways. In one embodiment, the pulsatile flow directed by the controller is synchronized to the measured EKG signals of the user. As used herein, the "pulse" refers to an increase in pump speed of a specified duration. For example, the duration of each pulse is determined based on the detected heart rate. In one embodiment, detection of a particular EKG feature (QRS complex, P-wave, T-wave, etc) serves as a trigger for the beginning and/or end of a pulse. In this way, the pulse dictated by the controller of the invention can be varied in real time, depending on the informational feedback loop of the changing heart rate of the user. In another embodiment, the pulsatile flow is determined by a simulated, desired, target, or commanded EKG signal. For example, the controller may use historical data or averaged data to simulate the EKG signal, which is then used to determine and direct the desired pulse parameters (e.g. timing, duration, etc.). In another embodiment, the pulsatile flow is asynchronous. For example, the heart rate and duration of systole can be manually set using the user interface of the external control unit. These imputed parameters, as well as the choice of co-pulsation or counter-pulsation, then are used by the controller to determine and direct the pulse parameters of the heart pump.

The source resonator may be placed anywhere in the vicinity of the user-implanted receiver resonator. For example, the source resonator can be worn on the body of the user, or placed in the same room or building of the user. In some embodiments, the wireless system comprises a plurality of receiver resonators, wherein the source receiver transfers power to a first receiver resonator, which transfers power to the next receiver resonator, and so forth. In some embodiments, the system comprises a plurality of receiver resonators, wherein the source receiver can transfer power to each of the plurality of receiver resonators. The frequency at which the source resonator resonates is adaptable, thereby allowing the powering of a plurality of receiver resonators, each of which is tuned to resonate at a specific frequency.

Figure 2:
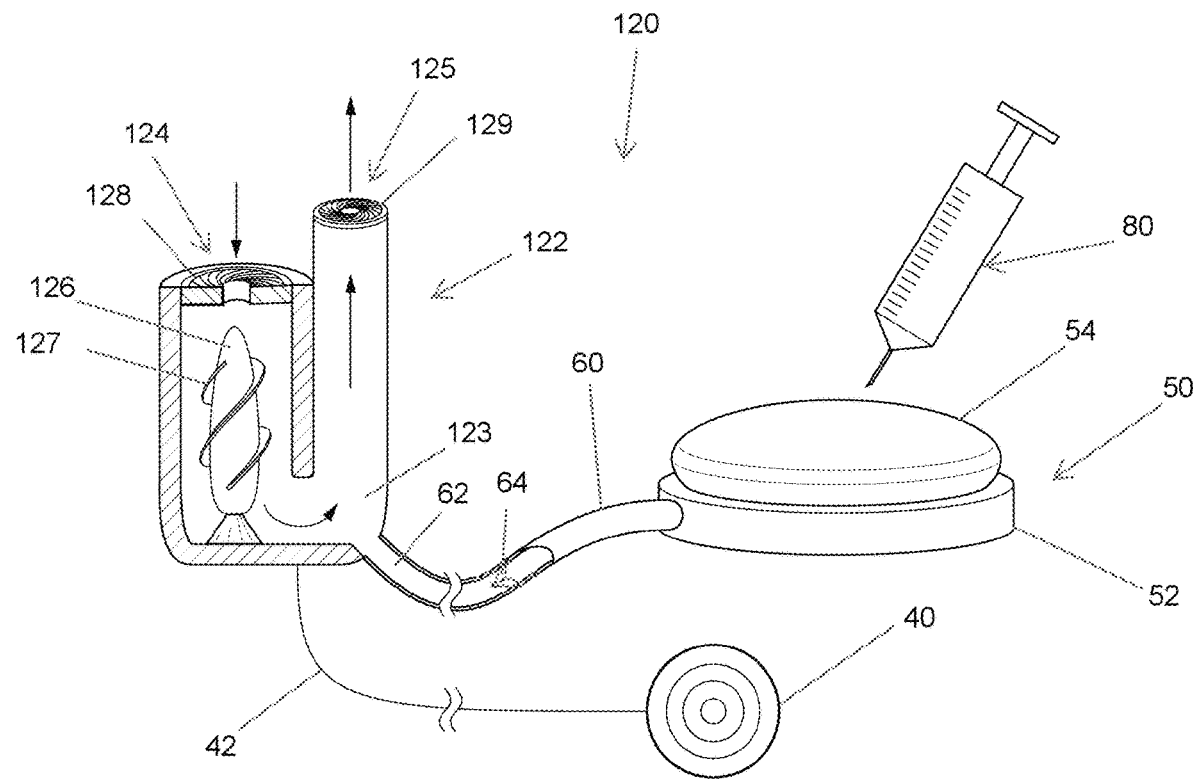
FIG. 2 is a partial cutaway view of the exemplary HFR device according to an aspect of the present invention.

With reference to FIG. 2, a HFR device 120 having a port 50 and receiver coil 40 attached is shown according to an exemplary embodiment of the invention. The fluid pump 122 includes an inlet 124 and an outlet 125, each fluidly sealed by an iris valve 128, 129. The iris valves 128, 129 can be programmed and operated by a controller to open while the pump 122 is actively pumping blood, and closed while the pump 122 is inactive, during periods of patient hemodynamic stability. In certain embodiments, the iris valve 128, 129 blades will be PTFE coated components and the opening and closing mechanism will be actuated by a small motor. In other embodiments, the valves are pressure actuated valves, such as one-way silicone duck bill valves directed along the inlet 124 or outlet 125 direction of blood flow, or slit valves. The pump 122 includes a pump element 126 having a spiraled protrusion 127 for moving fluid away from the inlet 124 and towards the outlet 125. When the pump element 126 rotates, the protrusion 127 will spin such that fluid will push down the reservoir 123 and towards the outlet 125.

An implantable port 50 is also included with the system in preferred embodiments. The implantable port 50 includes a housing 52 defining a reservoir, an opening to the reservoir fluidly sealed by an elastomeric needle-penetrable septum 54, and a fluid outlet stem for attachment to a flexible conduit 60, such as a catheter. An example of a conventional prior art port is described in a U.S. Pat. No. 4,673,394, the entire disclosure of which is incorporated herein by reference. The housing is typically made out of a medical grade plastic or metal alloy, such as titanium. The septum 54 is typically made from an elastomeric material, such as silicone, that will continue to reseal after multiple stick counts of the needle in the reservoir. When the port 50 is subcutaneously implanted in the patient, fluid from the needle 80 can be infused into the port 50 reservoir, and flushed into the catheter lumen 62 and subsequently into the reservoir of the fluid pump. As the catheter 60 is connected to the fluid pump 122 reservoir 123, an optional valve 64, such as a one-way pressure actuated duckbill valve can allow fluid to flow into the pump reservoir once a threshold fluid pressure is met, without allowing fluid to flow back towards the port. According to this embodiment, fresh exchanges of fluids such as saline can be introduced into the pump, post implantation, while the HFR device 120, including receiving coil 40 and implantable port 50 is completely subcutaneous. To help breakup or avoid a thrombus buildup in the pump reservoir 123 or at the openings of the valves 128, 129, the pump element 126 can be operated to momentarily spin in a reverse direction, shooting anticoagulant and cleansing fluid along the reserve direction, promoting breakup of blood formations. Alternatively, the pump element 126 can be programmed to agitate anticoagulant and cleansing fluid within the reservoir during maintenance, breaking-up any buildup of sludge or biological debris in corners of the reservoir 123 or on moving parts with a turbulent fluid dynamic.

Methods of interrogating, inspecting and manipulating heart pump function in situ can also be used, using a separate catheter. Guiding of these separate catheters to the heart pump can be done by any suitable method known in the art. For example, in one embodiment, the method comprises using the Seldinger technique for the insertion of a sheath into a blood vessel of a subject whose heart pump is being examined or manipulated. The inserted sheath then serves as an access point allowing for the introduction of one or more catheters, scopes, fluid delivery devices, and the like, into the blood vessel. The access point, where the sheath is inserted, may be located in any suitable location. For example, in certain embodiments, the access point for the sheath, catheter, or other components is the femoral artery in the subject's groin or in the radial artery in the subject's wrist. However, any suitable access point which provides access to the heart or heart pump may be used. A small steerable catheter can be passed from the femoral artery and threaded into the ascending aorta to the left ventricle. This catheter can then access the inflow port of an implanted heart pump. In certain embodiments, the catheter is a steerable catheter with a steering handle and bendable tip. However, any suitable catheter that may be steered to the heart or heart pump may be used. Alternatively, another catheter is guided to the outflow port of the heart pump. With the catheter in place, fluid and/or inspection devices can be introduced to clean and maintain the pump, and debris can also be aspirated from the interior and surfaces of the pump. In one embodiment, a balloon catheter is advanced to the inflow port or outflow port of the pump, and then inflated to manually disrupt thrombus formation at the valves.

As an exemplary method of treating heart failure, the pump is switched on when a decompensation phase is detected. This detection can be based, for example, on how the patient feels, a trigger from an ECG, or based on the opinion of a medical professional. When the pump is no longer needed and the patient reaches stable hemodynamics, it will be switched off. When switched off, at either end of the inflow and outflow there are electrically activated diaphragm valves, which will be activated, thus sealing the system. Once sealed, the injection port that is implanted under the skin will be accessed using a hypodermic needle. Through the injection port, any small amount of blood within the pump housing will be washed out using heparinized saline and ultimately the pump housing will be filled with remaining heparinized saline until the next use. At the next use of the pump when the patient presents with worsening heart failure symptoms, the subcutaneous port will be accessed similar to above, the pump housing will be cleaned with fresh saline or dextrose solution until the effluent is clear, and additional proteolytic enzymes can be used to make sure any residual protein debris are cleared. The hypodermic needle is then removed from the port, and the two diaphragm valves covering the inflow and outflow are opened. The pump is started and the patient begins to stabilize. A large population of heart failure patients need only a modest increase in cardiac index (CI), up to 1 L/m$^2$/min during the decompensation phases to avoid hospital readmission. This can be done as an outpatient procedure at regular intervals or when the patient indicates that they are not feeling well. Accordingly, readmissions to the hospital with heart failure can be minimized and avoided. The patient benefits with the completely subcutaneous design because they are less prone to infection given the absence of any medical components traversing the surface the skin, are more mobile, and do not have to worry about issues that conventional devices present, such as keeping external components dry. Physicians and health care institutions also benefit by increasing efficacy of infection and thrombus control, due to both the implantable nature of the system and the ability to introduce anticoagulants into the fluid reservoir, increasing the performance and reliability of the system, and representing a cost savings for medical institutions. Further, dangerous conditions associated with thrombus buildup are minimized, such as the introduction of emboli into the patient's system, or the malfunction or occlusion of device components.

Figure 3:
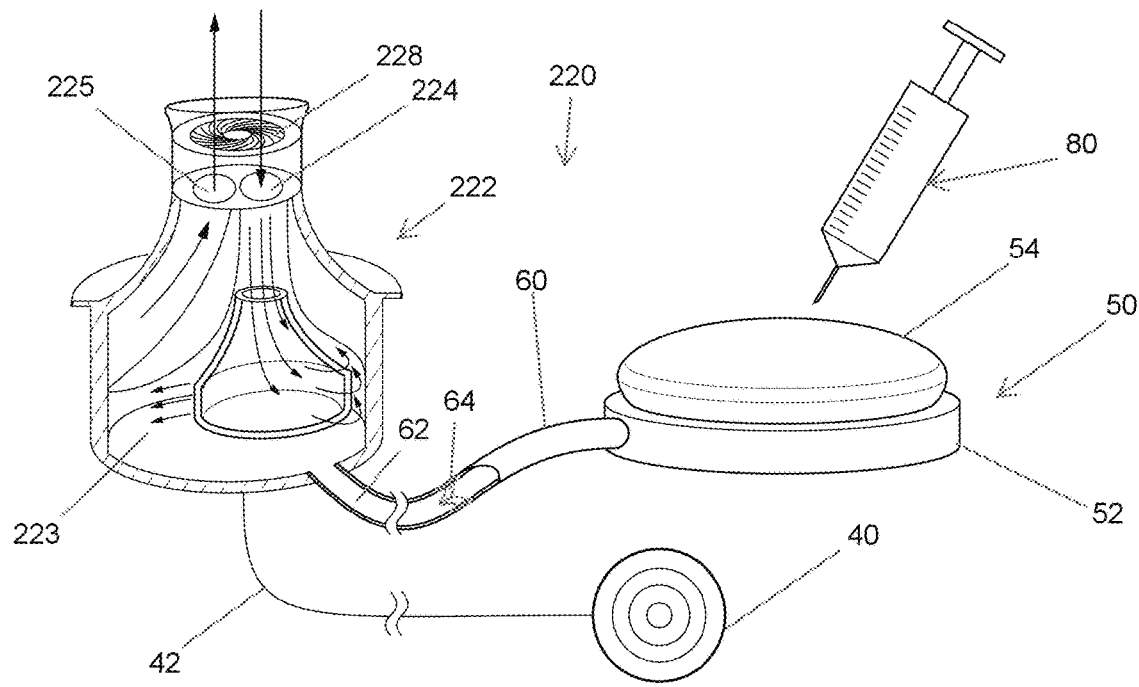
FIG. 3 is a partial cutaway view of another exemplary HFR device according to an aspect of the present invention.

An alternative pump embodiment is shown in FIG. 3. The HFR device 220 includes a fluid pump 222 having an inlet 224 and an outlet 225 communicating with the pump reservoir 223. The configuration of the implantable port 50 and the receiver coil 40 are similar to the configurations described above for previous embodiments. In this embodiment, an impeller draws fluid down into the reservoir 223, and channels fluid back up through a channel leading to the outlet 225. The outlet 225 can be joined up near the inlet 224 as needed to provide a desired step tip, staggered tip, split tip or even tip inlet/outlet configuration. A slot motor can be disposed within a casing as known in the art. An iris valve 228 seals fluid communication between the left ventricle and the heart when the HFR device 228 is inactive. The iris valve 228 can seal the entire fluid channel covering both the inlet and outlet as shown in FIG. 3, or alternatively, a first and second iris valve can be individually positioned at the inlet and outlet, similar to previous embodiments. The tangential position of the channel leading to the outlet 225, relative to the circular profile of the reservoir 223, allows for a superior flushing action, helping to combat the buildup of sludge and thrombus in the reservoir 223. The advantage of this geometric design along with the ability to introduce anticoagulants into the reservoir via the port helps to ensure reliable and efficient performance of the device, reducing the buildup of biological debris.

Partial support of 2-3 L/min can meaningfully affect the cardiac hemodynamics of heart failure patients. An operating range for the device in certain embodiments will output 0.5-3 L/min at pressures between 50-100 mmHg. The impeller diameter can vary, and in certain embodiments, will range from between 10-20 mm in diameter, with preferred embodiments at 15 mm in diameter. In certain embodiments, rotational speed of designs disclosed herein may range from 5,000 RPMs to 9,000, RPMs, with a preferred embodiment of about 7,000 RPMs.

The invention disclosed herein represents a paradigm shift in treating patients with heart failure. Most patients with heart failure require only a modest improvement in cardiac output from baseline to maintain hemodynamic stability over time. As such, full cardiac support in most heart failure patients is not needed to encourage recovery from heart failure, or as bridge to transplant or alternative heart failure therapy. The invention represents a minimally invasive and completely implantable system that can be activated as needed for ensuring a stable cardiac index, safely isolated from the circulatory system during hemodynamic recovery, and cleaned for future use.

What is claimed is:

1. A heart failure recovery device comprising:
   a fluid pump comprising an inlet and an outlet in fluid communication with a pump reservoir, and a pumping element disposed within the pump reservoir, the pumping element comprising a protrusion that in an active state is configured to rotate and move fluid away from the inlet and towards the outlet;
   a port comprising a port reservoir and a port opening fluidly sealed by an elastomeric septum; and
   a flexible conduit comprising at least one lumen;
   wherein the conduit is coupled to the fluid pump and the port, and
   wherein the port reservoir and the pump reservoir are in fluid communication via the at least one lumen; and
   wherein fluid moves from the port reservoir to the pump reservoir via one or more of the at least one lumen.

2. The heart failure recovery device of claim 1, wherein a pressure actuated valve is disposed across a portion of the at least one lumen.

3. A method for treating heart failure comprising:
   implanting a heart failure recovery device at the apex of a left ventricle of a human heart, the heart failure recovery device comprising:
      a fluid pump comprising an inlet and an outlet in fluid communication with a pump reservoir, and a pumping element disposed within the pump reservoir, the pumping element comprising a protrusion that in an active state is configured to rotate and move fluid away from the inlet and towards the outlet, and
      a port comprising a port reservoir and a port opening fluidly sealed by an elastomeric septum,
      wherein the port reservoir and the pump reservoir are fluidly connected by a flexible conduit comprising a lumen, and
      wherein the port reservoir is in fluid communication with the pump reservoir via the lumen;
   advancing a tip of a port access needle into the port reservoir;
   flushing a fluid from the port access needle into the port reservoir and the pump reservoir; and
   withdrawing the tip of port access needle from the port reservoir.

4. The method of claim 3 further comprising:
   detecting a first decompensation phase condition;

setting the fluid pump to the active state based on the detecting the first decompensation phase condition;

detecting a first stabilization condition; and setting the fluid pump to an inactive state based on the detecting the first stabilization condition.

5. The method of claim 4, wherein the fluid pump further comprises an opening in fluid communication with at least one of the inlet and the outlet, the opening fluidly sealed by a valve that opens in the active state and closes in the inactive state.

6. The heart failure recovery device of claim 1, further comprising a valve configured to open in the active state and fluidly seal at least one of the inlet and the outlet in an inactive state.

7. The heart failure recovery device of claim 6, wherein the valve is an iris valve.

8. The heart failure recovery device of claim 6, wherein the valve is configured to fluidly seal the inlet in an inactive state, and wherein a second valve is configured to fluidly seal the outlet in an inactive state.

9. The heart failure recovery device of claim 6, wherein the valve opens and closes in a substantially radial fashion.

10. A system comprising the heart failure recovery device of claim 1, the system comprising: an external coil configured to send electromagnetic energy to the receiver coil for powering the fluid pump while the receiver coil is implanted subcutaneously.

11. The heart failure recovery device of claim 1, wherein the pumping element comprises an impeller.

12. The heart failure recovery device of claim 1, wherein the pump reservoir has a substantially circular cross-sectional profile.

13. The heart failure recovery device of claim 1, wherein the elastomeric septum is a needle-penetrable elastomeric septum.

14. A heart failure recovery device comprising:

a fluid pump comprising an inlet and an outlet in fluid communication with a pump reservoir, and a pumping element disposed within the pump reservoir, the pumping element configured in an active state to and move fluid away from the inlet and towards the outlet;

a port comprising a port reservoir and a port opening fluidly sealed by an elastomeric septum; and a flexible conduit comprising at least one lumen;

wherein the conduit is coupled to the fluid pump and the port, and wherein the port reservoir and the pump reservoir are in fluid communication via the at least one lumen; and wherein fluid moves from the port reservoir to the pump reservoir via one or more of the at least one lumen.

15. The heart failure recovery device of claim 14, wherein a pressure actuated valve is disposed across a portion of the at least one lumen.

16. The heart failure recovery device of claim 14, further comprising a valve configured to open in the active state and fluidly seal at least one of the inlet and the outlet in an inactive state.

17. The heart failure recovery device of claim 16, wherein the valve is an iris valve.

18. The heart failure recovery device of claim 16, wherein the valve is configured to fluidly seal the inlet in an inactive state, and wherein a second valve is configured to fluidly seal the outlet in an inactive state.

19. The heart failure recovery device of claim 16, wherein the valve opens and closes in a substantially radial fashion.

20. A system comprising the heart failure recovery device of claim 14, the system comprising: an external coil configured to send electromagnetic energy to the receiver coil for powering the fluid pump while the receiver coil is implanted subcutaneously.

21. The heart failure recovery device of claim 14, wherein the pumping element comprises an impeller.

22. The heart failure recovery device of claim 14, wherein the pump reservoir has a substantially circular cross-sectional profile.

23. The heart failure recovery device of claim 14, wherein the elastomeric septum is a needle-penetrable elastomeric septum.

* * * * *